United States Patent [19]
Yardley

[11] 3,933,782
[45] Jan. 20, 1976

[54] (N-ACETYL)-PRO-D-PHE-TRP-SER-TYR-D-ALA-LEU-ARG-PRO-NHET AND INTERMEDIATES

[75] Inventor: John P. Yardley, King of Prussia, Pa.

[73] Assignee: American Home Products Corporation, New York, N.Y.

[22] Filed: Nov. 14, 1974

[21] Appl. No.: 523,953

[52] U.S. Cl. .................... 260/112.5 LH; 424/177
[51] Int. Cl.² .................. C07C 103/52; A61K 37/00
[58] Field of Search ......................... 260/112.5

[56] References Cited
OTHER PUBLICATIONS

Fujino et al.: Biochem. Biophys, Res. Comm., 57, 1248–1256 (1974).

Coy et al.: Biochem. Biophys. Res. Comm., 57, 335–340 (1974).

Fujino et al.: Biochem. Biophys. Res. Comm., 49, 863–869 (1972).

*Primary Examiner*—Lewis Gotts
*Assistant Examiner*—Reginald J. Suyat

[57] ABSTRACT

(N-Acetyl)-Pro-D-Phe-Trp-Ser-Tyr-D-Ala-Leu-Arg-Pro-NHEt, is described as well as its synthesis by solid phase techniques and novel intermediates formed by such synthesis. The novel non-apeptide exhibits and anti-ovulatory activity in mammals.

6 Claims, No Drawings

(N-ACETYL)-PRO-D-PHE-TRP-SER-TYR-D-ALA-LEU-ARG-PRO-NHET AND INTERMEDIATES

This invention relates to the novel nonapeptide (N-Acetyl)-Pro-D-Phe-Trp-Ser-Tyr-D-Ala-Leu-Arg-Pro-NHEt, its process of manufacture and novel intermediates formed in such synthesis.

The luteinizing hormone releasing factor (hereafter called LRF) is the decapeptide, L-(5-oxoprolyl)-L-histidyl-L-tryptophyl-L-seryl-L-tyrosyl-glycyl-L-leucyl-L-arginyl-L-prolylglycineamide. This decapeptide is secreted by the hypothalamus and carried to the adenohypophysis where it stimulates the release of the luteinizing hormone and the follicle stimulating hormone. Coy et al., Biochemistry, 13, No. 2. pp 323–26 (1974) describe [des-Gly$^{10}$]-LRF ethylamide, [des-His$^2$,-des-Gly$^{10}$]-LRF ethylamide and [des-Trp$^3$-des-Gly$^{10}$]-LRF ethylamide. In copending application Ser. No. 402,958 filed Oct. 3, 1973, now U.S. Pat. No. 3,855,199, there is described [D-Phe$^2$-D-Ala$^6$]-LRF as having anti-ovulatory activity.

The present invention concerns itself with structural modifications of LRF which exhibit anti-ovulatory activity.

The novel peptides of the present invention are represented by the compounds of the formula:

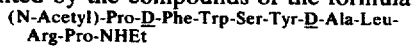

I and its non-toxic salts. All chiral amino acid residues identified in formula I supra, and the other formulas hereinafter are of the natural or L-configuration unless specified otherwise. The symbol "Et" means ethyl.

Also contemplated within the scope of the present invention are intermediates of the formula

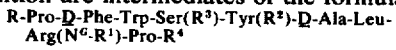

II wherein:

R is selected from the class consisting of hydrogen, acetyl and an α-amino protecting group. The α-amino protecting group contemplated by R are those known to be useful in the art in the step-wise synthesis of polypeptides. Among the classes of α-amino protecting groups covered by R are (1) acyl type protecting groups illustrated by the following: formyl, trifluoroacetyl, toluenesulfonyl (tosyl), nitrophenylsulfenyl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropyloxycarbonyl, allyloxycarbonyl; (4) cycloalkyl urethan type protecting groups illustrated by cyclopentyloxycarbonyl, adamantyloxycarbonyl, cyclohexyloxycarbonyl; and d-isobornyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R are selected from the class consisting of benzyloxycarbonyl, tert-butyloxycarbonyl, tert-amyloxycarbonyl and d-isobornyloxycarbonyl;

N$^G$ means the side chain nitrogen atoms of arginine; R$^1$ is a protecting group for the N$^δ$, N$^ω$ and N$^{ω'}$ nitrogen atoms of arginine selected from the class consisting of nitro, tosyl, benzyloxycarbonyl, and adamantyloxycarbonyl; or R$^1$ is hydrogen which means there are no protecting groups on the side chain nitrogen atoms of arginine. Where the protecting group is nitro or tosyl, the protection is on either one of the N$^ω$, N$^{ω'}$ nitrogens and in the case of benzyloxycarbonyl, or adamantyloxycarbonyl, the protection is on the N$^δ$ nitrogen and either one of the N$^ω$, N$^{ω'}$ nitrogen atoms. The preferred protecting group defined by R$^1$ is tosyl;

R$^2$ is a protecting group for the phenolic hydroxyl group of tyrosine selected from the group consisting of tetrahydropyranyl, tert-butyl, trityl, benzyl, 2,6-dichlorobenzyl, benzyloxycarbonyl and 4-bromobenzyloxycarbonyl. The preferred protecting group is 2,6-dichlorobenzyl or benzyl; R$^2$ is hydrogen which means there is no protecting group on the phenolic hydroxy function;

R$^3$ is a protecting group for the alcoholic hydroxyl group of serine and is selected from the group consisting of acetyl, benzyl, tetrahydropyranyl, tert-butyl, trityl, benzyl, 2,6-dichlorobenzyl or R$^3$ is hydrogen which means there is no protecting group on the alcoholic oxygen atom. Preferably R$^3$ is benzyl;

R$^4$ is selected from the group consisting of OH, N$_3$, NHNH$_2$, O-(lower)alkyl in which (lower)alkyl is C$_1$ through C$_6$ (e.g. methyl, ethyl, pentyl, isopropyl, hexyl, etc.), O-benzyl and an anchoring bond used in solid phase peptide synthesis linked to a solid polystyrene resin support represented by the formula:

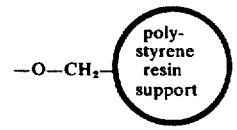

The polystyrene resin support is preferably a copolymer of styrene with about 1 to 2% divinyl benzene as a cross linking agent which causes the polystyrene polymer to be completely insoluble in most organic solvents. The polystyrene polymer is composed of long alkyl chains bearing a phenyl ring on every second carbon and the terminal amino acid residue (Pro) is joined through a covalent carbon to nitrogen or oxygen bond to these phenyl rings. The alkyl chains are cross linked at approximately every fiftieth carbon by p-substituted phenyl residues derived from divinyl benzene.

In selecting a particular side chain protecting group to be used in the synthesis of the peptides of formula (I), the following rules should be followed: (a) the protecting group must be stable to the reagent and under the reaction conditions selected for removing the α-amino protecting group at each step of the synthesis, (b) the protecting group must retain its protecting properties, (i.e. not be split off under coupling conditions), and (c) the side chain protecting group must be removable upon the completion of the synthesis containing the desired amino acid sequence under reaction conditions that will not alter the peptide chain.

Illustrative of pharmaceutically acceptable, non-toxic salts of formula I are hydrochloride, hydrobromide, sulfate, phosphate, maleate, acetate, citrate, benzoate, succinate, malate, ascorbate, and the like.

The nonapeptides of formulas (I) and (II) are prepared using solid phase synthesis. The synthesis is commenced from the C-terminal end of the peptide using an α-amino protected resin. Such a starting material can be prepared by attaching an α-amino protected proline to a chloromethylated resin or a hydroxymethyl resin, the former being preferred. The preparation of the hydroxymethyl resin is described by Bodanszky et al., Chem. Ind. (London) 38, 1597-98 (1966). A chloromethylated resin is commercially available from Bio Rad Laboratories Richmond, California and the preparation of such a resin is described by Stewart et al., "Solid Phase Peptide Synthesis" (Freeman & Co. San Francisco 1969), Chapter 1, pp 1-6.

The α-amino protected proline is coupled to the chloromethylated resin according to the procedure of Gisin, Helv. 56, p 1476 (1973). Following the coupling of the α-amino protected proline to the resin support, the α-amino protecting group is removed such as by using trifluoroacetic acid in dichloromethane, trifluoroacetic acid alone or HCl in dioxane. The deprotection is carried out at a temperature between about 0°C and room temperature. Other standard cleaving reagents and conditions for removal of specific α-amino protecting groups may be used as described in Schroder & Lubke, "The Peptides," 1 72-75 (Academic Press 1965). After removal of the α-amino protecting group the remaining α-amino protected amino acids are coupled step-wise in the desired order to obtain a compound of formula (I). However, as an alternate to adding each amino acid separately to the reaction, some of them may be coupled prior to addition to the solid phase reactor. Each protected amino acid or amino acid sequence, is introduced into the solid phase reactor in about a four-fold excess and the coupling is carried out in a medium of dimethylformamide: dichloromethane (1:1) or dimethylformamide or dichloromethane alone. In cases where incomplete coupling occurs the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence has been synthesized, the compound of formula I is preferably obtained by first acetylating with acetic anhydride to obtain (N-acetyl-Pro-D-Phe-Trp-Ser($R^3$)-Tyr($R^2$)-D-Ala-Leu-Arg($N^G$-$R^1$)-Pro-solid polystyrene resin support (IV) after which the protected peptide is removed from the resin by ammonalysis by treatment with ethylamine to obtain (N-acetyl)-Pro-D-Phe-Trp-Ser($R^3$)-Tyr($R^2$)-D-Ala-Leu-Arg($N^G$-$R^1$)-Pro-NHEt (V) after which the side chain protecting groups are cleaved by treatment of the nonapeptide of formula IV with hydrogen fluoride or other known prior art cleaving reagents to obtain a compound of formula I. Another route for obtaining the compound of formula I is to treat the acetylated and protected nonapeptide of formula IV with hydrazine in dimethylformamide to obtain N(acetyl)-Pro-D-Phe-Trp-Ser($R^3$)-Tyr($R^2$)-D-Ala-Leu-Arg($N^G$-$R^1$)-Pro-NHNH$_2$ (VI) which is converted to the corresponding azide by reaction with a reagent that will yield nitrous acid in situ. Suitable reagents for this purpose include a lower alkyl nitrite (e.g. isoamyl nitrite, tert-butyl nitrite) in the presence of a strong acid such as hydrochloride. This azide is then reacted with ethylamine to obtain a compound of formula V. Another alternate route for obtaining a compound of formula I is to simply cleave the acetylated protected nonapeptide of formula IV with hydrogen fluoride to obtain (N-acetyl-Pro-D-Phe-Trp-Ser-Tyr-D-Ala-Leu-Arg-Pro-OH (VII) after which this compound can be converted to a compound of formula I by activating the carboxyl group and then reacting the activated group with ethylamine. As an alternative to forming the free acid VII, a lower alkyl ester or benzyl ester can be formed such as by cleaving the peptide from the resin by methanolysis or by other means. A further alternative to obtaining the compound of formula I is to first obtain H-Pro-D-Phe-Trp-Ser-Tyr-D-Ala-Leu-Arg-Pro-NHEt and then acetylate with p-nitrobenzyl acetate. It should be apparent that the acetylation can be carried out either prior to or after removal of the protecting groups.

The following examples are illustrative of the preparation of the compounds of formulas I and II.

EXAMPLE 1

Preparation of tert-butoxycarbonylproline resin [method of Gisin, Helv, Chim. Acta, 56, 1476 (1973)]

tert-Butoxycarbonylproline (5.8 g., 27 mmoles) in an ethanol (35 ml.)-water (15 ml.) mixture is treated with concentrated aqueous cesium hydrogen carbonate solution until the pH of the solution reaches 7. The reaction mixture is stripped and dried by repeated stripping using ethanol, ethanol-benzene, benzent (three times). The foam residue is dried over phosphorus pentoxide, in vacuo at room temperature overnight.

The total product in dimethylformamide (275 ml.) is stirred overnight at 50°, under nitrogen, with Bio-Beads S.X. 1 Resin (chloromethylated capacity 0.89/meq./g.). The filtered resin is washed thoroughly with dimethylformamide (twice), dimethylformamide-10% water (twice), dimethylformamide (twice), methanol (twice), chloroform (thrice) and dried over $P_2O_5$. Amino acid analysis indicates a substitution on the resin of 0.64 meq./g.

In a similar experiment using chloromethylated resin with a capacity of 0.69 meq./g. a substitution of 0.5 meq./g. is obtained.

EXAMPLE 2

N-Acetyl-L-propyl-D-phenylalanyl-L-tryptophyl-O-benzyl-L-seryl-O,2,6-dichlorobenzyl-L-tyrosyl-D-alanyl-L-leucyl-$N^g$-tosyl-L-arginyl-L-prolyl acyl resin ester t-Boc-prolyl acyl resin ester (20 g.) obtained in Example 1 in a Merrifield vessel is treated to the following wash cycle (a) methylene chloride-trifluoroacetic acid prewash (5 minutes), (b) methylene chloride-trifluoroacetic acid (2 × 15 minutes), (c) methylene chloride (twice), (d) dimethylformamide, (3) dimethylformamide — 12.5% triethylamine (2 × 10 minutes), (f) dimethylformamide, (g) methylene chloride (twice), (h) methanol (twice), (i) methylene chloride (thrice), allowing a contact time of at least 3 minutes each if not indicated otherwise.

The resin so prepared is gently shaken with t-Boc-$N^a$-tosyl arginine (25 meq.) in 1:1 methylene chloride-dimethylformamide during 5 minutes followed by the addition of 1M dicyclohexylcarbodiimide (25 ml., 25 meq.) in two portions 30 minutes apart. Shaking is continued during 18 hours. The peptide resin is washed successively with (j) methanol, (k) methylene chloride, (l) methanol (twice), (m) methylene chloride (twice). Normally to test for completeness of reaction, the peptide-resin is subjected to a ninhydrin test following the procedure of E. Kaiser et al., Analytical Biochemistry 34, 595 (1970). Proline, however, is anomalous giving a weak color reaction in the above test so that coupling is repeated using 8.3 mmoles t-Boc-N$^g$-tosyl-arginine and 8.3 mmoles DCC.

The following amino acid residues are introduced sequentially onto a washed (steps (j)–(m), deprotected and neutralized, steps (a)–(i)) peptide resin, t-Boc-L-leucine hydrate (25 meq.), t-Boc-D-alanine (25 meq.), t-Boc-0-2,6-dichlorobenzyl-L-tyrosine (25 meq.), t-Boc-0-benzyl-L-serine (25 meq.), t-Boc-L-tryptophan (25 meq.). All couplings are mediated using 25 meq. 1M dicyclohexylcarbodiimide in methylene chloride as described for the addition of t-Boc-N$^g$-tosyl-arginine except for the case of t-Boc-L-leucine, the DCC reagent being added first to reduce the possibility of peptide loss via diketo piperazine formation, cf. B. F. Gisin & R. B. Merrifield, J. Amer. Chem. Soc., 94, 3102 (1972). At this point, the washed and dried resin weighs 30 g. The synthesis is continued with 3.5 g. peptide-resin, t-Boc-L-proline (5 meq.) and 5 meq. 1M dicyclohexylcarbodiimide in methylene chloride as described above but modified by the addition of 5% (volume) of ethane-dithiol to deprotection steps (a) and (b) for this and in the terminal acylation sequence. The washed peptide-resin is deprotected and neutralized steps (a)–(i), washed with dimethylformamide and acetylated by shaking with acetic anhydride (5 ml.) and triethylamine (7.6 ml.) in dimethylformamide during 3 hours. The resin is washed with dimethylformamide (thrice), CH$_2$Clhd 2, methanol (thrice), CH$_2$Cl$_2$ (thrice) and dried to give the above-titled product.

EXAMPLE 3

N-Acetyl-L-prolyl-D-phenylalanyl-L-tryptophyl-O-benzyl-L-seryl-O,2,6-dichlorobenzyl-L-tyrosyl-D-alanyl-L-leucyl-N$^g$-tosyl-L-arginyl-N-ethyl-L-prolinamide Protected peptide-resin (ca. 3.7 g.) from Example 2 and ethylamine (120 ml.) are stirred overnight in a glass pressure bottle, Ethylamine is removed under reduced pressure and the residue is washed with methanol, dimethylformamide (four times), methanol and methylene chloride. The combined filtrates are evaporated in vacuo below 35°C to give, after reprecipitation from methanol solution with ether, the above-titled compound (0.9 g.).

EXAMPLE 4

N-Acetyl-L-prolyl-D-phenylalanyl-L-tryptophyl-L-seryl-L-tyrosyl-D-alanyl-L-leucyl-L-arginyl-N-ethyl-L-prolinamide The product of Example 3 (0.9 g.) is treated in vacuo with anhydrous liquid hydrogen fluoride (60 ml.) and anisole (15 ml.) for 1 hour at 0°C. Hydrogen fluoride is removed under reduced pressure and the residue distributed between ether and 10% aqueous acetic acid, both layers are backwashed with the other solvent and the combined aqueous extracts lyophilized to afford the crude above-titled compound.

The total product is applied to a column (100 × 2 ½ cm.) of Sephadex G-15 fine previously equilibrated with aqueous acetic acid (33 1/3%). Peptide material is located by Ehrlich spot test and UV analysis at 280 mµ. One major fraction (dropmeter setting 200 drops/tube), tubes 28–40 (600 mg.), are obtained. The product is rechromatographed on a partition column of Sephadex G-25 fine, (prepared by equilibration with lower phase and then upper phase of the system, n-butanol:acetic acid:water, 4:1:5). Elution with upper phase affords a fraction located as above in tubes (dropmeter setting 240 drops/tube) 43–55 (250 mg.).

The following R$_f$'s are obtained in 2 different solvent systems by thin layer chromatography on silica: n-butanol:acetic acid:water (4:1:5, upper phase), 0.55; n-butanol:pyridine:acetic acid:water (5:5:1:3) 0.77; n-butanol:ethyl acetate:acetic acid: water (1:1:1:1) .36. [α] ΣD25 −41.8 (c, 1.038, 1% HOAc).

Amino acid analysis of the peptide hydrolyzed in 6N HCl containing 4% thioglycollic acid for 20 hours at 110°C in a closed system under nitrogen gave: Ser (.98); Pro (2.0); Ala (1.0); Leu (.99); Tyr (.93); Phe (.98); Trp (.83); Arg (-not significant due to overlap with EtNH$_2$ peak).

The compounds of formula I possess anti-ovulatory activity and hence are potentially useful in inhibiting fertility in female mammals. In tests conducted with female rats (225 to 250 grams body weight) complete ovulation inhibition was achieved in 80% of the rats tested at a dose of about 12 mg/kg. The test was conducted with mature Sprague-Dawley rats, normally cycling, unanesthetized, proestrous rats. On the afternoon of proestrous, each rat in the test group received six subcutaneous injections of the acetate salt of formula I in corn oil, each injection being given a half hour following the previous injection. The rats are sacrificed the next morning and the number of animals ovulating and the number of ova shed are recorded following the procedure described by E. S. France, Neuroendocrinology 6, pp 77–89 (1970). The absence of or a significant decrease in the number of ova is the criterion for an anti-ovulation effect. At a dose of 1 mg per injection inhibition of ovulation was achieved in 80% of the rats tested. In contrast the nonapeptide p-Glu-D-Phe-Trp-Ser-Tyr-D-Ala-Leu-Arg-Pro-NHEt was found to be devoid of antiovulatory activity in the foregoing test.

The compounds of formula I can be administered to mammals intravenously, subcutaneously, intramuscularly or orally for fertility inhibition and control. The effective dosage will vary with the form of administration and the particular species of mammal to be treated. A typical dosage is a physiological saline solution containing a compound of formula I administered in a dose range of between about 20 to 30 mg/kg of body weight. Oral administration may be in either solid or liquid form.

What is claimed is:

1. A compound selected from the group consisting of (N-Acetyl)-L-Pro-D-Phe-L-Trp-L-Ser-L-Tyr-D-Ala-L-leu-L-Arg-L-Pro-NHEt and its non-toxic salts.

2. A compound selected from the group consisting of R-L-Pro-D-Phe-L-Trp-L-Ser(R$^3$)-L-Tyr(R$^2$)-D-Ala-L-Leu-L-Arg(N$^G$-R$^1$)-L-Pro-R$^4$ and their salts; wherein:

R is selected from the class consisting of hydrogen, acetyl and an α-amino protecting group;

R$^1$ is selected from the class consisting of hydrogen and a protecting group for the N$^δ$, N$^ω$ and N$^{ω'}$ nitrogen atoms of arginine selected from nitro, tosyl, benzyloxycarbonyl and adamantyloxycarbonyl;

R$^2$ is selected from the class consisting of hydrogen and a protecting group for the phenolic hydroxyl group of tyrosine selected from tetrahydropyranyl, tert-butyl, trityl, benzyl, 2,6-dichlorobenzyl, benzyloxycarbonyl and 4-bromobenzyloxycarbonyl;

R$^3$ is selected from the class consisting of hydrogen and a protecting group for the alcoholic hydroxyl group of serine selected from the group acetyl, benzoyl, tetrahydropyranyl, tert-butyl, trityl, benzyl and 2,6-dichlorobenzyl; and $R^4$ is selected from the group consisting of Oh, $NHNH_2$, $N_3$, O-(lower)alkyl, 0-benzyl and an anchoring bond used in solid phase peptide synthesis linked to a solid resin support represented by

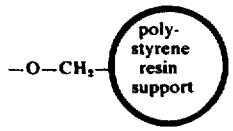

wherein said polystyrene is cross linked through the phenyl group on each second carbon atom of the alkyl chain of said polystyrene.

3. A compound according to claim 2 wherein $R^4$ is represented by said solid polystyrene support.

4. A compound according to claim 3 wherein R is acetyl.

5. A compound according to claim 4 wherein $R^1$ is tosyl, $R^2$ is 2,6-dichlorobenzyl and $R^3$ is benzyl.

6. A compound according to claim 2 wherein R is hydrogen, each of $R^1$, $R^2$ and $R^3$ is a protecting group and $R^4$ is represented by said solid polystyrene resin.

* * * * *